United States Patent
Majeed et al.

(10) Patent No.: US 9,833,422 B2
(45) Date of Patent: Dec. 5, 2017

(54) ANTI-CANCER ACTIVITY OF (E)-1-(3',4'-DIMETHOXYPHENYL)BUTADIENE

(71) Applicants: Muhammed Majeed, Edison, NJ (US); Kalyanam Nagabhushanam, East Windsor, NJ (US)

(72) Inventors: Muhammed Majeed, Edison, NJ (US); Kalyanam Nagabhushanam, East Windsor, NJ (US)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 15/361,053

(22) Filed: Nov. 24, 2016

(65) Prior Publication Data

US 2017/0196820 A1    Jul. 13, 2017

Related U.S. Application Data

(60) Provisional application No. 62/275,847, filed on Jan. 7, 2016.

(51) Int. Cl.
*A61K 31/09*    (2006.01)

(52) U.S. Cl.
CPC .................................. *A61K 31/09* (2013.01)

(58) Field of Classification Search
None
See application file for complete search history.

(56) References Cited

PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*

* cited by examiner

*Primary Examiner* — Kristin Vajda

(57) ABSTRACT

The present invention provides a method of using (E)-1-(3', 4'-dimethoxyphenyl) butadiene to induce anti-tumorigenic effects in pancreatic carcinoma, ovarian carcinoma and prostate carcinoma. The invention also provides a method of using (E)-1-(3', 4'-dimethoxyphenyl) butadiene to prevent cancer metastasis.

2 Claims, 6 Drawing Sheets

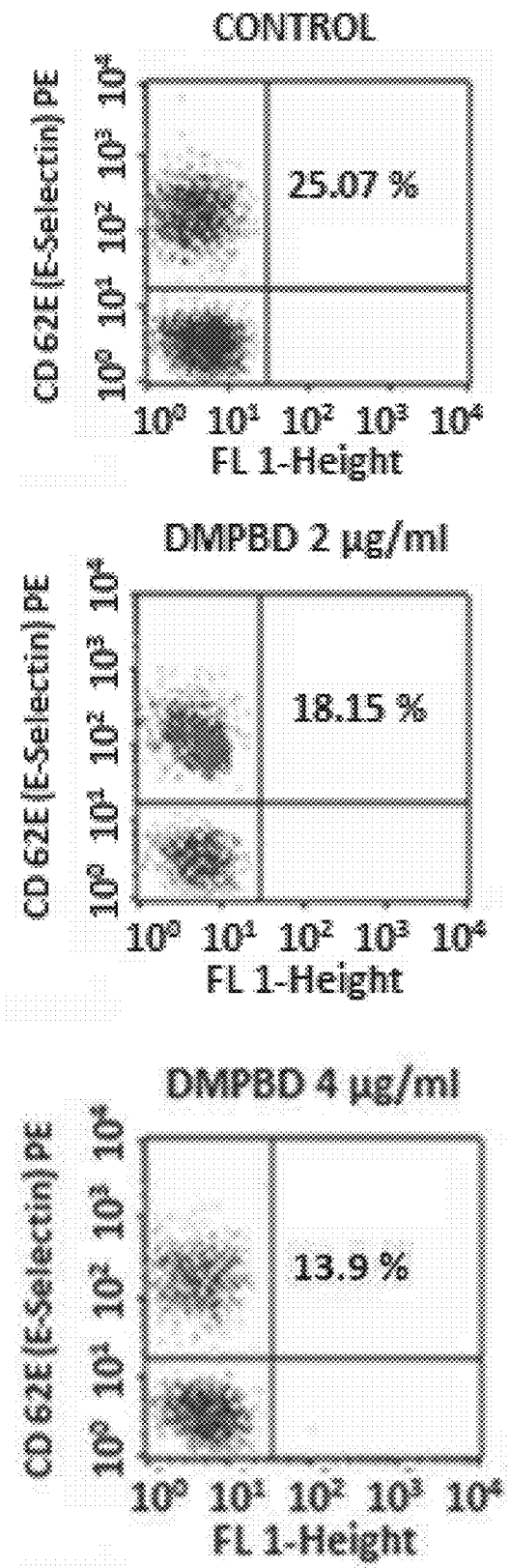

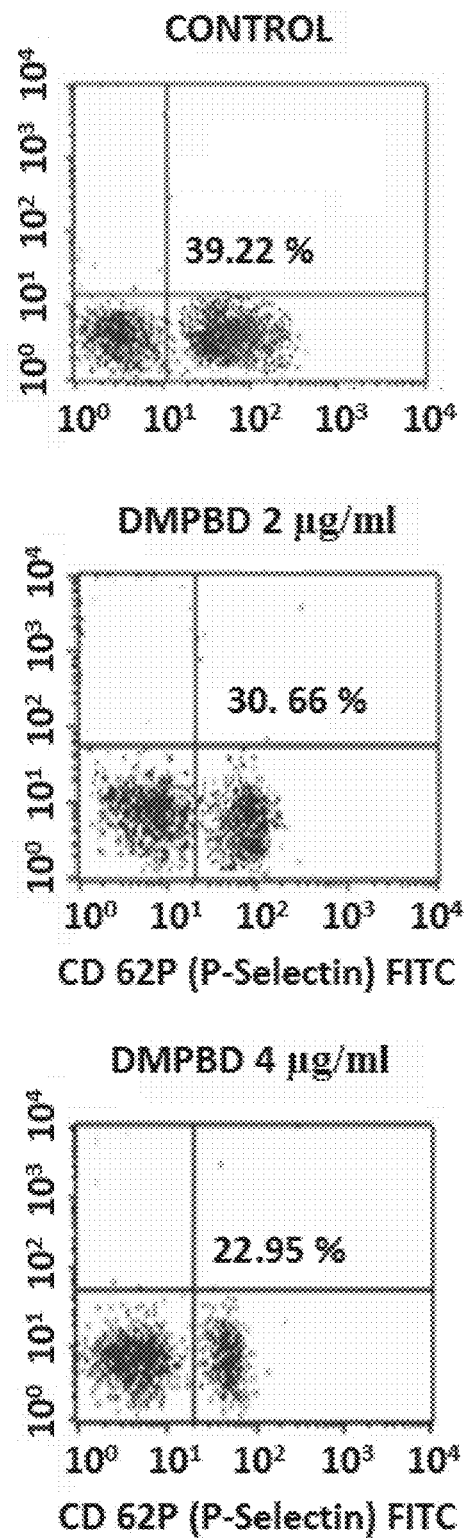

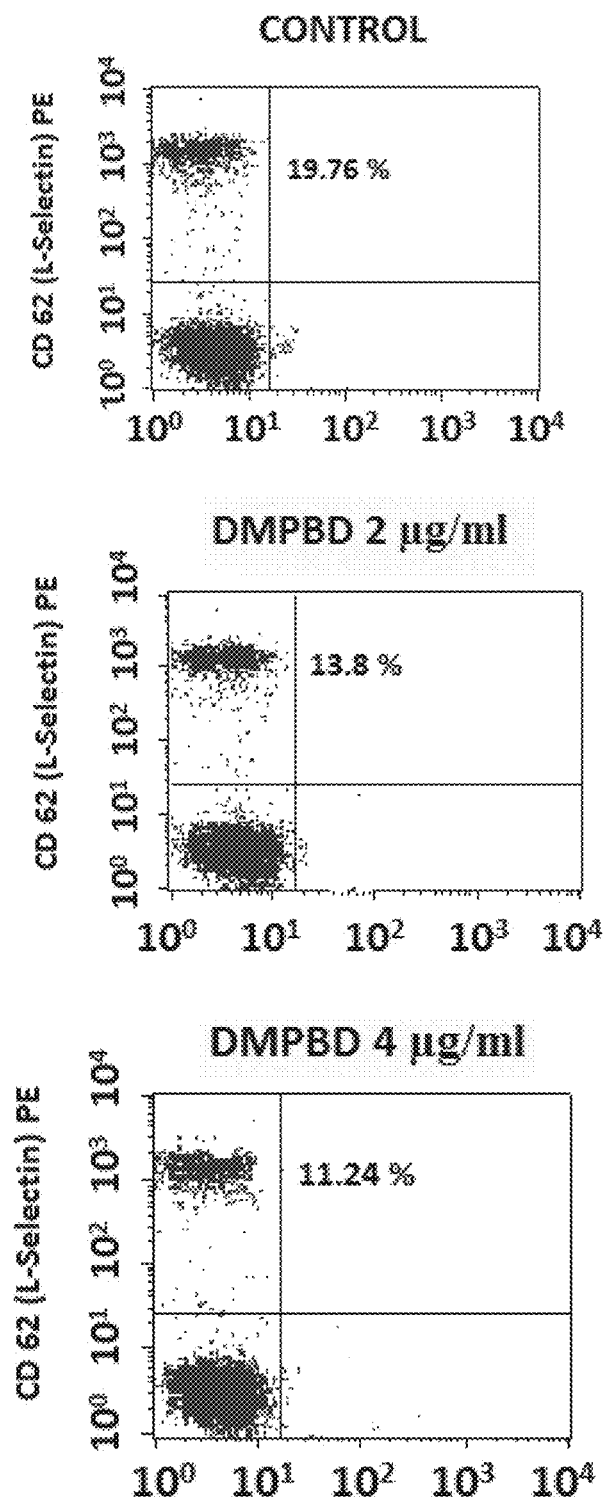

ANTI-CANCER ACTIVITY OF (E)-1-(3',4'-DIMETHOXYPHENYL)BUTADIENE

CROSS-REFERENCE TO RELATED PATENT APPLICATION

This is a non-provisional patent application claiming priority from U.S. Provisional Patent Application No. 62/275,847 filed on 7 Jan. 2016.

BACKGROUND OF THE INVENTION

Field of the Invention

The invention in general relates to cancer therapeutics. More specifically, the present invention relates to the ability of (E)-1-(3', 4'-Dimethoxyphenyl) butadiene [DMPBD] to exert anti-tumorigenic and anti-metastatic activity.

Description of Prior Art

It is well known that chronic inflammation increases the risks of cancer and eliminating inflammation reduces the risk for cancer development. Hence anti-inflammatory agents are encouraged to be used in tandem (as adjuvants) with chemotherapeutic agents wherein these anti-inflammatory agents exert their activity by reducing toxicity of associated chemotherapy, by altering the pharmacokinetics chemotherapeutics resulting in better efficacy and due elimination and also by sensitising cancerous cells to chemotherapy itself (Elizabeth R. Rayburn et al, "Anti-inflammatory agents for cancer chemotherapy", Mol Cell Pharmacol. 2009; 1 (1): 29-43. It is also known from prior art that anti-inflammatory substances can also have anti-cancer effects. For example, Nonsteroidal anti-inflammatory drugs (NSAIDS induce apoptosis in various cancer cells. Despite many suggested mechanisms for the anti-cancer effect of NSAIDS including cyclooxygenase inhibition, reactive oxygen species inhibition, and NF-κB mediated signal inhibition, it remains uncertain how they induce cell cycle arrest and apoptosis in cancer cells. In other words, there is little information on the selectivity of anti-inflammatory agent mediated anti-cancer effects although this information is very critical for successful anti-cancer therapy and future cancer therapeutic advances (M. Adachi et al, "Nonsteroidal anti-inflammatory drugs and oxidative stress in cancer cells", Histol Histopathol (2007) 22: 437-442). Thus, the prediction of the direct effect of such anti-inflammatory molecules in cancer growth or metastasis is difficult (Laurie E Walker, "NSAIDS as anticancer drugs", in clinician's brief) and needs considerable scientific evaluation. The anti-inflammatory properties of (E)-1-(3,4-dimethoxyphenyl) butadiene (DMPBD) is well known from prior art (Jeenapongsa et al, "Anti-inflammatory activity of (E)-1-(3, 4-dimethoxyphenyl) butadiene from Zingiber cassumunar Roxb.", J Ethnopharmacol. 2003 August;87(2-3):143-8), Also, the efficacy o the trans dimer of DMPBD namely, (+/−) trans-3-(3', 4'-dimethoxyphenyl)-4-[(E)-3''', 4'''-dimethoxy-styryl] cyclohex-1-ene has been discussed in terms of its antiproliferative effects in lung cancer (Journal of Pharmacognosy and Phytochemistry 2015; 4(1): 01-06).

The present inventors for the first time demonstrate the concentration dependant in-vitro anti-tumorigenic activity of (E)-1-(3,4-dimethoxyphenyl) butadiene on cancer cell lines PANC-1 (pancreatic carcinoma), DU-145 (prostate carcinoma) and SKOV3 (ovarian carcinoma) through cell proliferation assays. Further, the unique ability of DMPBD to cause significant fold decrease in the expression of cell adhesion molecules (P-selectin, E-selectin and L-selectin) as evaluated by flow cytometric studies on pancreatic carcinoma cells points to the molecule's specific function as an anti-metastatic agent. Important prior art emphasising the role of selectins in tumor metastasis include.

a. H. Laubli et al, "Selectins promote tumor metastasis", Semin Cancer Biol. 2010 June; 20 (3): 169-77;
b. Hariri. G et al, "Radiation guided P-selectin antibody targeted to lung cancer", Ann Biomed Eng. 2008 May; 36 (5): 821-830;
c. Chen M et al, "P-selectin mediates adhesion of leucocytes, platelets and cancer cells in inflammation, thrombosis, cancer growth and metastasis", Arch Immunol Ther Exp (Warsz). 2006 March-April; 54 (2): 75-84; and
d. Okegawa T et al, "The role of cell adhesion molecule in cancer progression and its application in cancer therapy", Acta Biochim Pol. 2004; 51 (2) 445-57.

These scientific developments are important given that cancer therapy objective depends on 1. Specificity of chemotherapeutic agent to a particular cancer type; and
2. Twin efficacy of said agent in preventing undue cell proliferation and also tumor metastasis.

The inventive features of the present invention as elucidated above clearly fulfill the aforesaid objectives by demonstrating the anti-tumorigenic specificity of DMPBD for pancreatic, ovarian and prostate carcinomas and also the ability of DMPBD to prevent spread or metastasis of these carcinomas or others by inhibition of cell adhesion molecules p-selectin, E-selectin and L-selectin thus providing novel and non-obvious technical information useful for chemotherapy of pancreatic, ovarian and prostate cancers and prevention of metastasis thereof.

SUMMARY OF THE INVENTION

The present invention pertains to the anti-tumorigenic and anti-metastatic properties of (E)-1-(3', 4'-Dimethoxyphenyl) butadiene [DMPBD]. Specifically, the invention discloses the anti-tumorigenic properties of DMPBD against pancreatic carcinoma, prostate carcinoma and ovarian carcinoma. Further, the invention also discloses the ability DMPBD to cause significant fold decrease in the expression of cell adhesion molecules (P-selectin, E-selectin and L-selectin) as evaluated by flow cytometric studies on pancreatic carcinoma cells. The latter studies discloses the anti-metastatic property of DMPBD.

The advantages of the present invention includes the disclosure of the anti-tumorigenic specificity of DMPBD for pancreatic, ovarian and prostate carcinomas and also the ability of DMPBD to prevent spread or metastasis by inhibition of cell adhesion molecules P-selectin, E-selectin and L-selectin.

Other features and advantages of the present invention will become apparent from the following more detailed description, taken in conjunction with the accompanying images, which illustrate, by way of example, the principle of the invention.

Figure 1:
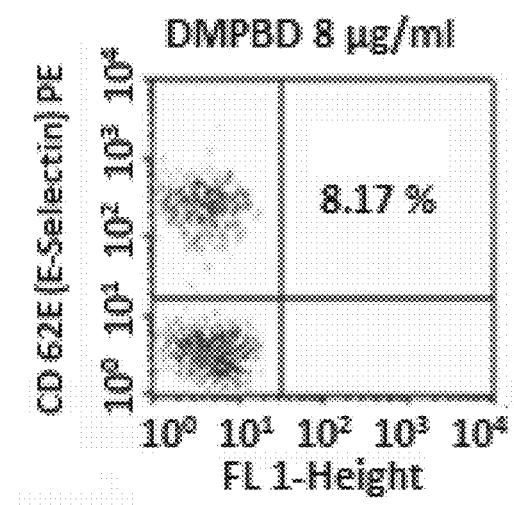
FIG. 1 shows the effect of DMPBD in reducing the expression of adhesion molecule E-selectin (CD 62E).
Figure 1:
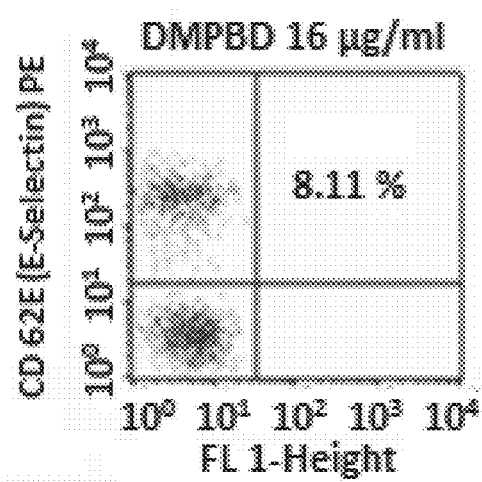
Figure 2:
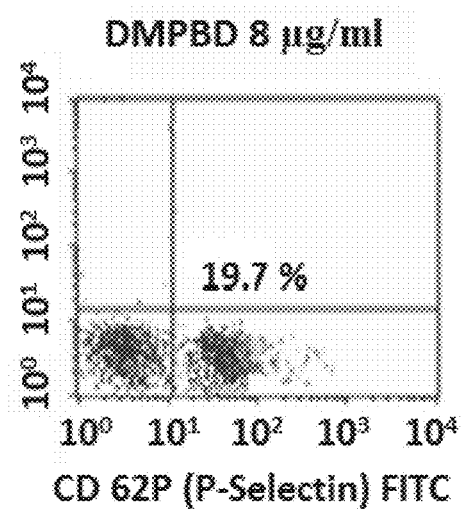
FIG. 2 shows the effect of DMPBD in reducing the expression of adhesion molecule P-selectin (CD 62P).
Figure 2:
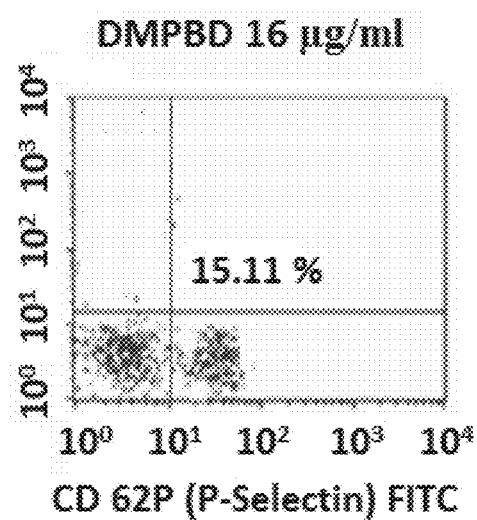
Figure 3:
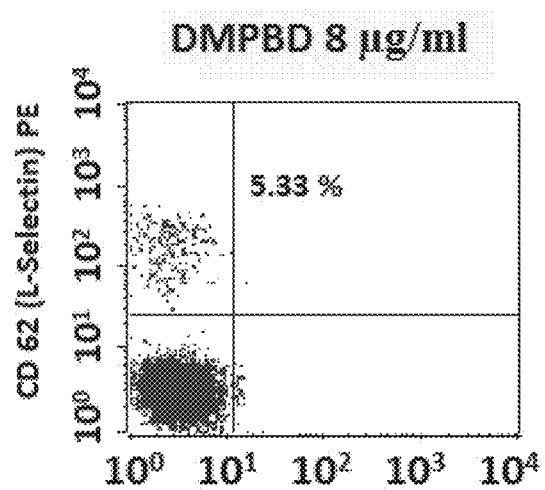
FIG. 3 shows the effect of DMPBD in reducing the expression of adhesion molecule L-selectin (CD 62L).
Figure 3:
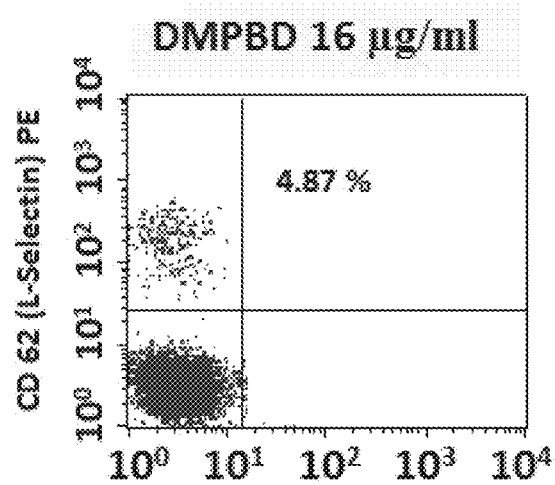

DESCRIPTION OF THE MOST PREFERRED EMBODIMENTS (FIG. 1, FIG. 2 and FIG. 3)

In the most preferred embodiment, the present invention relates to a method of inducing anti-tumorigenic effect on human cancer cells, said method comprising step of treating said cancer cells with effective amount of (E)-1-(3', 4'-Dimethoxyphenyl) butadiene. In preferred embodiments, said human cancer cells are selected from group consisting of prostate carcinoma cells, ovarian carcinoma cells and pancreatic carcinoma cells.

In another most preferred embodiment, the present invention relates to a method of inhibiting the progression and metastasis of human cancer cell, said method comprising step of treating said cancer cell with effective amount of (E)-1-(3', 4'-Dimethoxyphenyl) butadiene to bring about the effect of significant reduction in cell adhesion molecule expression thereby inhibiting cancer progression and metastasis. In preferred embodiments, the cell adhesion molecule is selected from group consisting of P-selectin, E-selectin and L-selectin.

In yet other most preferred embodiments, the present invention relates to
1. (E)-1-(3', 4'-Dimethoxyphenyl) butadiene for use in a method of treating pancreatic carcinoma.
2. (E)-1-(3', 4'-Dimethoxyphenyl) butadiene for use in a method of treating ovarian carcinoma.
3. (E)-1-(3', 4'-Dimethoxyphenyl) butadiene for use in a method of treating prostate carcinoma.
4. (E)-1-(3', 4'-Dimethoxyphenyl) butadiene for use in treating cancer metastasis wherein (E)-1-(3', 4'-Dimethoxyphenyl) butadiene arrests metastasis by inhibiting the expression of cell adhesion molecules selected from group consisting of P-selectin, E-selectin and L-selectin.
5. Compositions comprising (E)-1-(3', 4'-Dimethoxyphenyl) butadiene in effective amounts for use in a method of treating pancreatic carcinoma.
6. Compositions comprising (E)-1-(3', 4'-Dimethoxyphenyl) butadiene in effective amounts for use in a method of treating ovarian carcinoma.
7. Compositions comprising (E)-1-(3', 4'-Dimethoxyphenyl) butadiene in effective amounts for use in a method of treating prostate carcinoma.
8. Compositions comprising (E)-1-(3', 4'-Dimethoxyphenyl) butadiene in effective amounts for use in a method of arresting cancer metastasis by inhibiting the expression of cell adhesion molecules selected from group consisting of P-selectin, E-selectin and L-selectin.
9. Use of (E)-1-(3', 4'-Dimethoxyphenyl) butadiene in effective amounts for the manufacture of a medicament for use in treatment of pancreatic carcinoma.
10. Use of (E)-1-(3', 4'-Dimethoxyphenyl) butadiene in effective amounts for the manufacture of a medicament for use in treatment of ovarian carcinoma.
11. Use of (E)-1-(3', 4'-Dimethoxyphenyl) butadiene in effective amounts for the manufacture of a medicament for use in treatment of prostate carcinoma.
12. Use of (E)-1-(3', 4'-Dimethoxyphenyl) butadiene in effective amounts for the manufacture of a medicament for use in arresting cancer metastasis by inhibiting the expression of cell adhesion molecules selected from group consisting of P-selectin, E-selectin and L-selectin.

Specific illustrative examples enunciating the most preferred embodiments are included herein below.

EXAMPLE 1

In-Vitro Anti-tumorigenic Effect of DMPBD on Human Cancer Cell Lines

Human pancreatic PANC-1 cancer cell line (pancreatic carcinoma cells), human prostate DU145 cancer cell line (prostate carcinoma) and human ovarian cancer SKOV3 (ovarian carcinoma) cell line were grown and cultured using standard protocols known in the art. The cancer cell lines were treated with DMPBD in varying concentrations for measuring cytotoxicity. The estimation of the viability assay of the cells was done by the MTT (3-(4,5-dimethylthiazol-2-yl)-2,5-diphenyltetrazolium bromide) colorimetric assay. The MTT Assay measures the cell proliferation rate and conversely, when metabolic events lead to apoptosis or necrosis, the reduction in cell viability. The data is analyzed by plotting cell number versus absorbance allowing the quantification of changes in cell proliferation. The rate of tetrazolium reduction is proportional to the rate of cell proliferation.

Calculation:

Cytotoxicity of the sample is expressed as $IC_{50}$ value, the concentration which inhibits 50% of the cell growth.

$$\% \text{ Cytotoxicity} = (E-T/E) \times 100$$

Where,
E=Cell viability in the absence of the sample.
T=Cell viability in the presence of the sample The MTT Assay as performed was adapted from (1) Tim Mosmann. Rapid Colorimetric Assay for Cellular Growth and Survival: Application to Proliferation and Cytotoxicity Assays. Journal of Immunological Methods, 65 (1983) 55-63; (2) A. A. van de Loosdrecht, R. H. J. Beelen, G. J. Ossenkoppele, M. G. Broekhoven, M. M. A. C. Langenhuijsen. A tetrazolium-based colorimetric MTT assay to quantitate human monocyte mediated cytotoxicity against leukemic cells from cell lines and patients with acute myeloid leukemia. Journal of Immunological Methods 174 (1994) 311-320 and Denis Gerlier and Nicole Thomasset. Use of MTT colorimetric assay to measure cell activation. Journal of Immunological Methods, 94 (1986) 57-63.

Results

TABLE 1

| Ser. No. | Cell Lines | Description | $IC_{50}$ (µg/ml) |
|---|---|---|---|
| 1 | PANC-1 | Pancreatic carcinoma | 4.2 |
| 2 | DU 145 | Prostate carcinoma | 8.6 |
| 3 | SKOV3 | Ovarian carcinoma | 13.5 |

EXAMPLE 2

Effect of DMPBD on the expression of adhesion molecules E-selectin, P-selectin and L-selectin (anti-metastatic effect of DMPBD)-ILLUSTRATIVE EXAMPLE ON PANCREATIC CARCINOMA CELLS (FIG. 1, FIG. 2 and FIG. 3)

Plating of the Pancreatic carcinoma cells was done. The confluent cultures were harvested by trypsinization and expanded during two more passages before they were used for the experiments. Medium and other culture components were renewed after 48-72 h. All cell cultures were maintained at 37° C. in 95% air and 5% CO2 in a CO2 incubator.

10 ng/ml of recombinant human TNF-alpha and IL-1beta was added to the cell culture. DMPBD was added at graded concentration. After 72 hours the cells were incubated with specific antibodies PE labeled CD 62E; FITC labeled CD 62P and PE labeled CD 62L in different sets for 5 hours. The cells were then trypsinised and acquired on Flow cytometer for analyzing the effect of DMPBD. The Flow cytometric analysis was adapted from the teachings of (1) Carvers J, de Wildt-Eggen J, Heeremans J, Scharenberg J, de Korte D, van der Meer P F. Flow cytometric measurement of CD62P (P-selectin) expression on platelets: a multicenter optimization and standardization effort. Transfusion. 2008. 48(7): 1439-46, (2) Choi Y W. Kim H J. Park S S. Chung H W. Lee S O. Oh B S. Kim J B. Kim H Y. Chung B P. Yu C D. Kim S Y. Inhibition of endothelial cell adhesion by the new anti-inflammatory agent alpha-iso-cubebene. Vascul Pharmacol. 2009;51:215-224 and (3) Yen Y T, Liao F, Hsiao C H, Kao C L. Chen Y C, Wu-Hsieh B A. Modeling the early events of severe acute respiratory syndrome coronavirus infection in vitro. J Virol. 2006 March;80(6):2684-93.

DMPBD used in the aforesaid experiments was obtained from the rhizomes of Zingiber cassumunar by proprietary process, the steps of which are highlighted herein below.
1. Pulverized material of Z. cassumunar rhizome was extracted with methanol (4 vol×4) with constant stirring at 60-70° C. The methanolic extract was pooled and concentrated.
2. The concentrate of step 1 was then washed with hexane (4 vol×4) at 55-60° C. and resultant product (hexane extract) pooled and concentrated;
3. The hexane extract of step 2 was then solubilised in methanol and mixed with γ-cyclodextrin in a ratio of 2:3 with proper refluxing and vacuum dried at 55-60° C. to yield 90% water soluble final product with yield 7.79% and assay of DMPBD 10.73% and assay of DMPB-1-en 0.44%.

While the invention has been described with reference to a preferred embodiment, it is to be clearly understood by those skilled in the art that the invention is not limited thereto. Rather, the scope of the invention is to be interpreted only in conjunction with the appended claims.

We claim:
1. A method of inducing anti-tumorigenic effect on prostate carcinoma cells, ovarian carcinoma cells or pancreatic carcinoma cells, said method comprising step of treating said cells with effective amount of (E)-1-(3',4'-Dimethoxyphenyl)butadiene.
2. A method of inhibiting the progression and metastasis of pancreatic carcinoma cells, said method comprising step of treating said pancreatic carcinoma cells with effective amount of (E)-1-(3',4'-Dimethoxyphenyl)butadiene to bring about the effect of significant reduction in cell adhesion molecule expression thereby inhibiting carcinoma progression and metastasis wherein cell adhesion molecule is selected from group consisting of P-selectin, E-selectin and L-selectin.

* * * * *